United States Patent

Mattingly, III

[11] Patent Number: 5,694,739
[45] Date of Patent: Dec. 9, 1997

[54] ABSORBENT ARTICLES WITH INTEGRAL RELEASE SYSTEM AND METHODS OF MAKING SAME

[75] Inventor: William B. Mattingly, III, Ithaca, N.Y.

[73] Assignee: McNeil-PPC, Inc., Skillman, N.J.

[21] Appl. No.: 438,285

[22] Filed: May 10, 1995

Related U.S. Application Data

[62] Division of Ser. No. 935,145, Aug. 24, 1992, Pat. No. 5,591,153, which is a continuation of Ser. No. 569,103, Aug. 17, 1990, abandoned.

[51] Int. Cl.$^6$ .................................................. B65B 63/04
[52] U.S. Cl. ...................................................... 53/429
[58] Field of Search ................... 53/429, 117; 493/334, 493/405, 416, 254; 604/904, 386, 387, 389, 390; 206/363, 440; 156/226, 227, 289, 291

[56] References Cited

U.S. PATENT DOCUMENTS

| | | | |
|---|---|---|---|
| 2,693,439 | 11/1954 | Blanchard et al. | 167/84 |
| 3,638,651 | 2/1972 | Torr | 128/284 |
| 3,950,824 | 4/1976 | Karami | 24/67 |
| 3,994,299 | 11/1976 | Karami | 128/287 |
| 4,010,753 | 3/1977 | Tritsch | 128/284 |
| 4,024,867 | 5/1977 | Mesek | 128/287 |
| 4,040,424 | 8/1977 | Hunt | 128/290 |
| 4,085,754 | 4/1978 | Ness et al. | 128/287 |
| 4,122,552 | 10/1978 | Tedford | 604/390 |
| 4,286,595 | 9/1981 | Ring | 128/263 |
| 4,336,804 | 6/1982 | Roeder | 128/290 |
| 4,337,772 | 7/1982 | Roeder | 128/290 |
| 4,376,440 | 3/1983 | Whitehead et al. | 604/387 |
| 4,380,450 | 4/1983 | Reich | 604/386 |
| 4,555,022 | 11/1985 | Eagon et al. | 206/440 |
| 4,589,876 | 5/1986 | Van Tilburg | 604/385 |
| 4,596,570 | 6/1986 | Jackson et al. | 604/387 |
| 4,608,047 | 8/1986 | Mattingly | 604/387 |
| 4,690,680 | 9/1987 | Higgins | 604/386 |
| 4,699,792 | 10/1987 | Nick et al. | 424/446 |
| 4,701,178 | 10/1987 | Glaug et al. | 604/387 |
| 4,725,468 | 2/1988 | McIntyre | 428/40 |
| 4,781,712 | 11/1988 | Barabino et al. | 604/385.1 |
| 4,815,457 | 3/1989 | Mazars et al. | 206/440 |
| 4,832,008 | 5/1989 | Gilman | 206/440 |
| 4,862,574 | 9/1989 | Seidy | 29/415 |
| 4,917,675 | 4/1990 | Taylor et al. | 206/440 |
| 4,917,929 | 4/1990 | Heinecke | 428/41 |
| 4,960,417 | 10/1990 | Tarr, Jr. et al. | 604/15 |
| 4,985,025 | 1/1991 | Lingertat et al. | 604/390 |

(List continued on next page.)

FOREIGN PATENT DOCUMENTS

| | | |
|---|---|---|
| 182 692 A1 | 5/1986 | European Pat. Off. . |
| 313426 A1 | 4/1989 | European Pat. Off. . |
| 2086742 | 12/1971 | France . |
| 1416936 | 10/1968 | Germany . |
| 2049493 | 4/1971 | Germany . |
| 3326026 A1 | 2/1985 | Germany . |

OTHER PUBLICATIONS

EP 91 11 3865 EPO Search Report.
EP 91 11 3866 EPO Search Report.
EP 91 30 7580 EPO Search Report.
EP 91 30 75 81 EPO Search Report.

*Primary Examiner*—John Sipos
*Assistant Examiner*—Ed Tolan

[57] ABSTRACT

Absorbent articles such as panty liners, thin full-sized sanitary napkins and the like having a garment facing side and a body facing side are provided which may be stored in a folded configuration prior to use. Means of attachment and means of release, most preferably silicone, are created on the garment facing side of the article. The patterns in which the attachment and release means are chosen such that when the article is folded, the adhesive means contact the release means, eliminating the need for release paper, but allowing the article to be unfolded and used. Other embodiments using barrier films affixed to the garment facing side of the article are also disclosed. Methods of making and packaging the articles disclosed are also provided.

3 Claims, 2 Drawing Sheets

U.S. PATENT DOCUMENTS

| | | | |
|---|---|---|---|
| 5,046,608 | 9/1991 | Laipply | 206/209 |
| 5,066,289 | 11/1991 | Polski | 604/389 |
| 5,088,993 | 2/1992 | Gaur | 604/385.1 |
| 5,106,383 | 4/1992 | Mulder et al. | 604/389 |
| 5,106,384 | 4/1992 | Polski | 604/390 |
| 5,125,918 | 6/1992 | Seidy | 604/386 |
| 5,133,705 | 7/1992 | Nakanishi et al. | 604/387 |
| 5,217,448 | 6/1993 | Glaug et al. | 604/397 |
| 5,413,568 | 5/1995 | Roach et al. | 206/440 |
| 5,423,737 | 6/1995 | Cartmell et al. | 206/440 |
| 5,478,336 | 12/1995 | Pigneul | 604/387 |

ABSORBENT ARTICLES WITH INTEGRAL RELEASE SYSTEM AND METHODS OF MAKING SAME

This is a division of application Ser. No. 07/935,145 now U.S. Pat. No. 5,591,153, filed Aug. 24, 1992, which is a continuation application of Ser. No. 07/569,103, filed Aug. 17, 1990 abandoned, which are hereby incorporated by reference.

The present invention relates to improved absorbent articles. More particularly, the present invention relates to sanitary napkins, panty liners and the like having integral adhesives for affixing the absorbent article to a user's undergarment.

BACKGROUND OF THE INVENTION

Absorbent articles such as panty liners and sanitary napkins are well known throughout the art. Generally, these articles have an absorbent, body facing side and a garment facing side. In many instances, the garment facing side is comprised of a fluid impermeable barrier film. A preferred method of securing these articles so that there is close, direct contact between the perineal area and the user's undergarment is to apply an adhesive to the garment facing side. The adhesive is chosen to provide sufficient anchoring strength to hold the article firmly in place while the user moves.

Inherent in absorbent articles of the above-described construction is the requirement to have release paper applied to the adhesive. The release paper allows the article to be manufactured, packaged, stored, and otherwise handled without the adhesive adhering to itself or any other object. Release paper also serves to prevent oxidation, dust or dirt contamination of the adhesive and evaporation of tackifying resins. Unfortunately, the use of release paper is undesirable for several reasons. First, before the absorbent article can be used, the paper must be removed and discarded. This presents disposal problems and reduces the discretion with which the absorbent articles may be used. Second, release paper adds significantly to product cost. This is particularly true for low cost panty liners and the like which use very little absorbent material. Extra costs due to the release paper are incurred by both the additional material costs and the additional processing time and labor required to apply the release paper.

Thus, it would be desirable to eliminate the need for release paper while still retaining the adhesive applied to the garment facing side of an absorbent article so that it can be used to adhere the absorbent article the undergarment during use but will not stick to itself or an inappropriate surface before use.

SUMMARY OF THE INVENTION

Accordingly, it has now been found that the need for release paper may be eliminated using the method and products of this invention. More particularly, the elimination of release paper may be accomplished by creating release zones and attachment zones. Within the attachment zones are located attachment means. Within the release zones are located release means. The attachment and release means are placed such that when the subject absorbent articles is folded along at least one fold line, the attachment means meet with the release means.

In accordance with this invention, absorbent articles, such as panty liners and the like, are provided which are capable of being stored in a folded configuration prior to use. These absorbent articles have a body-facing. Side and a garment-facing side. Preferably, attachment zones and release zones are created on the garment facing side of the article. Release means may be created by depositing a release agent within the release zone, e.g., by coating at least a portion of the release zone with a release agent. Most preferably, the release agent is silicone, although it may be any of a number of chemical release agents known to those skilled in the art. However, a release agent need not be deposited to create release means. Alternatively, the release means may simply constitute designated areas of the garment-facing side of the absorbent article when the garment-facing side of the absorbent article is made of an appropriate material which can act as a release means.

Attachment means are preferably created on the garment facing side of the article by delineating attachment zones and depositing attachment or adhesive means to at least a portion of the attachment zones. These attachment zones may be treated to make them more receptive to the attachment means. The attachment means may consist of any means of releasably attaching the absorbent article known to those skilled in the art, for example, pressure-sensitive adhesives, Velcro™ type hook-and-loop attachment or non-slip materials or the like. For the sake of clarity, the following descriptions will exemplify embodiments employing pressure-sensitive adhesive attachment means, however, the description will apply equally to other attachment means.

The patterns in which the adhesive and release means are applied are chosen so that when the article is folded, the attachment means contact the release means, eliminating the need for release paper, but allowing the article to be unfolded and used. The garment facing side of the products of this invention on which the attachment and release zones are located may be polyolefin (e.g., polyethylene or polypropylene) films, non-wovens or the like.

Regardless of the type of attachment means used, the attachment means must bond more strongly to the attachment zone than to the user's undergarment and/or to the release means; the release means must bond more strongly to the release zone than it does to the attachment means and/or to the undergarment; and the attachment means must not bond so strongly to the undergarment that it rips or damages the undergarment by depositing adhesive means on the undergarment.

According to the method of making the products of this invention, there is provided an absorbent article which may be folded along at least one fold line, which remains in the folded position during storage, opens upon demand and which can be attached to the crotch portion of an undergarment. Furthermore, the method and products of this invention permit the wearer to disengage the article from the undergarment without depositing attachment means on the undergarment or tearing the undergarment or the absorbent article.

The ability to accomplish this objective is achieved by controlling the differential "bond strength" with respect to each surface to which the attachment means and the release means are adhered. "Peel strength" is a measurement of the strength of an adherent bond. Peel strength is measured in force per unit of width, i.e., the force required to separate adherently joined materials per unit of width. Preferably, a high peel or bond strength should be present between the attachment means and the attachment zones on the garment facing side of the articles of this invention. Likewise, a high peel or bond strength should be present between the release means and the release zones on the garment facing side of the articles of this invention.

A relatively lower peel strength should be present between the release means and the attachment means such that they may be separated prior to use. The differential peel strengths permit the articles of this invention to be stored in a folded position, opened at will without damaging the absorbent article and adhered to an undergarment without damaging the undergarment or absorbent article upon removal.

DETAILED DESCRIPTION OF THE PREFERRED EMBODIMENTS

Figure 1:
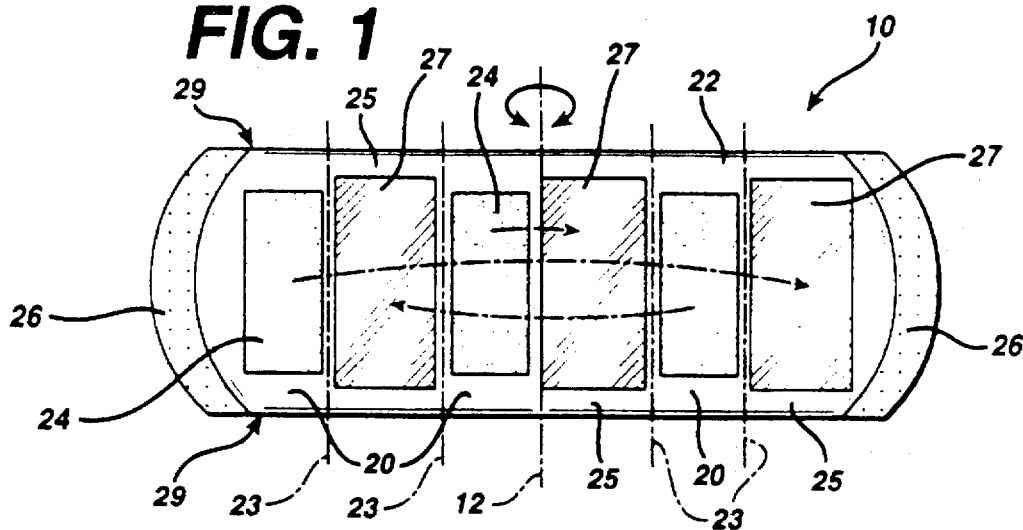
FIG. 1 is a plan view of the garment-facing side of a panty liner made in accordance with the present invention.

The present invention eliminates the need for release paper by providing release means and attachment means in the respective release and attachment zones delineated on the garment-facing side of an absorbent article. According to one preferred embodiment, the attachment means are in the form of an adhesive coating. In this embodiment, the release means should have a low enough peel strength with respect to the adhesive coat so as to separate from the adhesive coat without causing damage by stripping adhesive from the attachment zones. The adhesive coat used should have a high enough peel strength with respect to the attachment zone of the garment facing side of the absorbent article to provide sufficient anchorage to prevent adhesive transfer from the article to the undergarment when removing the product from the undergarment after use.

Most preferably, the zones of release and attachment are chosen so that when the product is folded, the adhesive means applied in an attachment zone is covered by the release means within a release zone.

A number of methods may be used to impart the required peel strength characteristics to different zones on the garment facing side of an absorbent article. One method is to use a coating of silicone release agent as the release means applied in the release zones. The attachment zones are left untreated with the silicone coat, and adhesive is applied to at least a portion of the untreated areas. Preferably, the release means are larger in area than the adhesive means such that the adhesive means and release means have a tolerance available for slight folding errors or means placement errors. Preferably, an area of the attachment zones peripherally surrounding the area to which the adhesive is applied may be left uncovered by adhesive. This creates a space around the adhesive such that when the panty liner is folded, there is some tolerance within which the areas of adhesive can avoid contacting the other adhesive means. Furthermore, this provides tolerance for slight errors in adhesive placement within the attachment zone.

Many types of barrier films may be used on the undergarment-facing side of the absorbent to create or allow the creation of attachment and/or release means on that side of the absorbent. For example, the barrier film may be made of polypropylene, high density polyethylene, low density polyethylene, linear low density polyethylene, cellophane, polyvinyl acetate, polyvinyl alcohol, polycaprolactan, polyester, polytetrafluoroethylene (Teflon®), or mixtures or coextrusions of one or more of these materials. Additionally, films made of materials synthesized to facilitate high moisture vapor transmission could also be used. Highly calendered paper or nonwoven material may also be substituted for films. Further, additives may be combined with the film resin to control the peel or bond strength of the film-to-adhesive bond.

In addition to the above, certain materials, such as Teflon®, produce inherently low adhesive-to-film peel strengths. For these materials, a release coating may not be required in the release zones. Instead, treatment may be necessary to increase the adhesive-film bond in the zones to which adhesive is to be applied. A low-peel strength substrate may be embossed to provide more anchorage surface for the adhesive, or selectively corona treated. The zones to which adhesive will be applied could be either chemically etched or altered to otherwise impart a stronger adhesive-film bond in the attachment zone. In certain embodiments, the adhesive can be applied at a temperature high enough to partially melt the film and produce a "weld" between the film and the adhesive, thereby obviating the need for a separate treatment.

A preferred method of surface treatment is corona treatment of the barrier film which forms the garment facing side of the absorbent article. Corona treatment involves the application of a large voltage across the surface of the film. The resulting treated surface is very reactive and permits the film to form chemical, as well as mechanical, bonds with coatings applied to the surface of the treated article. This provides firmer attachment of both the adhesive and the silicone release coating to the barrier film.

For purposes of securing the absorbent product to the user's undergarment, a wide variety of positioning adhesives are available, pressure sensitive hot melt adhesives being the most widely used and most preferred. These adhesives may be A-B-A block copolymers or the like, such as styrene-ethylene-butylene-styrene block copolymer, e.g., Stereon, or a diblock AB styrene butadiene adhesive. Hot melt adhesives such as HM-6513 or 1972 from H. B. Fuller (St. Paul, Minn.) or N.S. 34-5509 from National Starch (Bridgewater, N.J.) are good candidates. Of course, adhesives other than hot melt adhesives may also be used and should be chosen based on the numerous factors such as the compatibility of the adhesives with the other materials being used and the end use of the absorbent product.

The products of this invention may also be made by providing a roll of film which is coated with silicone on one side and adhesive on the other. Strips of this silicone-coated "tape" may be placed on one side of another film which has adhesive on both sides. The tape can be placed in an appropriate pattern (silicone side exposed) against the double adhesive coated film so that the adhesive of one side meets adhesive of the other. This will bond the tape to the film and produce areas of silicone release on the film, i.e., release means. The areas not covered with the tape become the attachment means. Patterns of release and attachment means can be configured such that, when folded, the attachment means is covered by release means.

FIG. 1 illustrates one of the preferred embodiments of the product of this invention. Panty liner 10 has two transverse edges 26 and two longitudinal edges 29. Panty liner 10 also has one or more attachment zones 20 bounded by imaginary lines 23 delineated on its garment facing side 22. Release zones 25 are also bounded by lines 23. As illustrated, adhesive is applied to attachment zones 20 to create adhesive means 24, in an alternating pattern with release zones 25. Release zones 25 may be coated over their entire areas with a release agent, such as silicone to create release means 27. Choosing the patterns of adhesive means 24 within attachment zones 20 and release means 27 within release zones 25 so that they will contact each other when the article is folded eliminates the need for release paper on the garment facing side of panty liner 10. Release means 27 must completely cover adhesive means 24. Thus, as shown in FIG. 1, each attachment zone 20 is placed in an alternating pattern with a release zone 25 arranged about the transverse central fold-line 12 such that the adhesive zones 20 cannot register with each other. Thus, as shown in FIG. 1 each attachments means 20 is placed in an alternating pattern with a release means 27 arranged about the transverse central fold-line 12 such that the usable surface of the adhesive means contacts only the release means. The usable surface of the attachment means is the surface which normally contacts the undergarment during use. Transverse central fold-line 12 need not be a defined fold, but is an imaginary line extending along the transverse axis of the panty liner along which the liner may be folded. Furthermore, the line along which the absorbent article of this invention may be folded need not be transverse or central. Alternatively, fold lines may be located along one or more transverse lines or may be located along one or more longitudinal or even diagonal lines.

Figure 2:
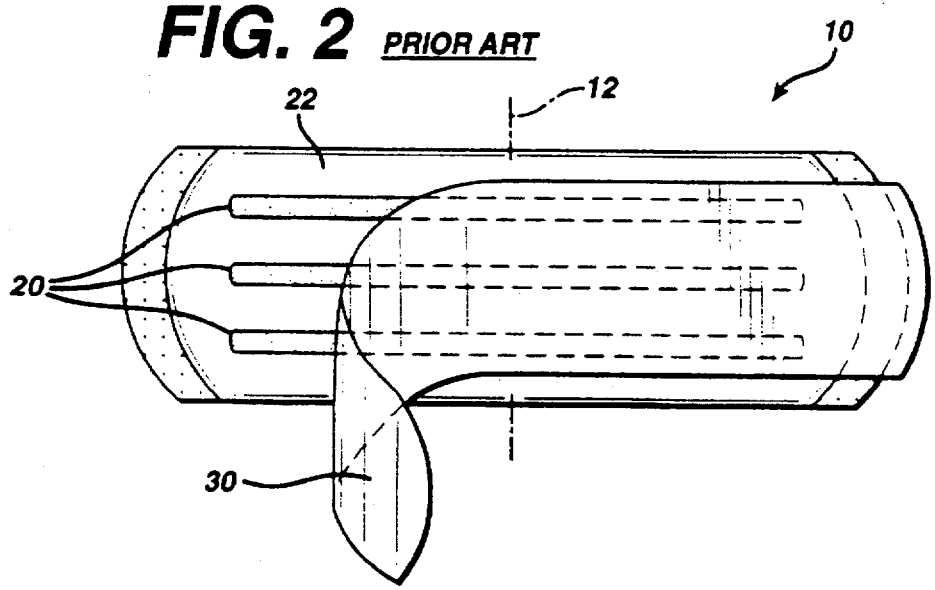
FIG. 2 is a plan view of the garment-facing side of a typical panty liner, showing the release paper partially removed.

FIG. 2 depicts a panty liner 10 of a construction known within the art. Panty liner 10 typifies the kind of absorbent product to which the present invention may be applied. Panty liner 10 has two transverse ends 26 and two longitudinal edges 27. A panty liner of the type illustrated in FIG. 2 typically has one or more adhesive zones 20 applied to the garment facing side 22. The adhesive zone 20 is usually covered with release paper 30, shown partially removed or "peeled back" in FIG. 2. The use of a release paper 30 allows an absorbent article such as the panty liner illustrated to be folded along one or more fold lines. Release paper 30 is used to protect the positioning adhesive zone 20 from dusk and other contaminants and from oxidation. For illustration, the transverse central fold-line 12 illustrated in FIG. 2 is designated as such a fold line. Without the use of release paper 30, panty liner 10 could not be folded along the transverse central fold-line 12 to bring the garment facing side into contact with itself, since adhesive 20 would adhere to itself and/or other portions of the garment facing side 22.

Figure 3:
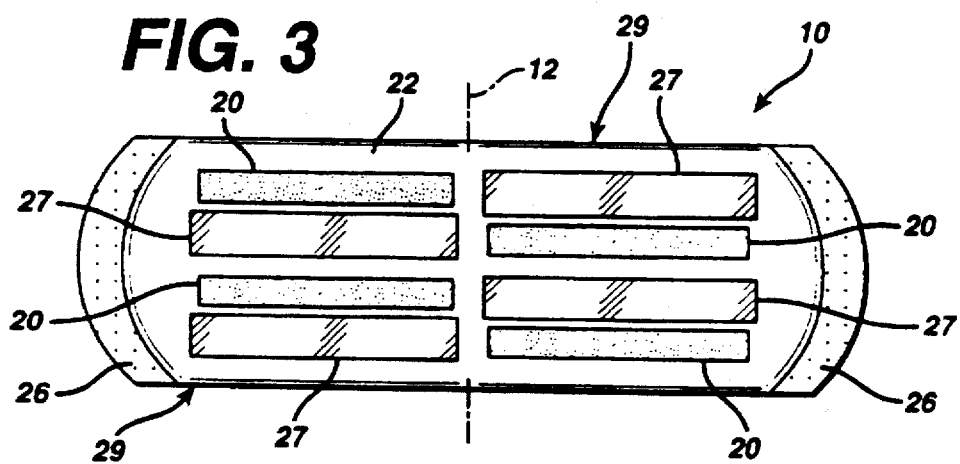
FIG. 3 is a plan view of an alternate embodiment of the panty liner depicted in FIG. 1.

An alternate embodiment of the present invention is illustrated in FIG. 3. In this embodiment, adhesive means 20 and release means 27 are applied to a panty liner 10 along its longitudinal axis. However, the panty liner is still intended to be folded about its transverse central fold-line 12. As illustrated, adhesive means 20 and release means 27 alternate on both sides of the central fold-line so that when the panty shield is folded, the adhesive means contact the release means. In this Figure, the boundaries of the attachment and release zones are not identified to clarify the diagram, although one could easily envision where the zone boundaries lie.

Figure 4:
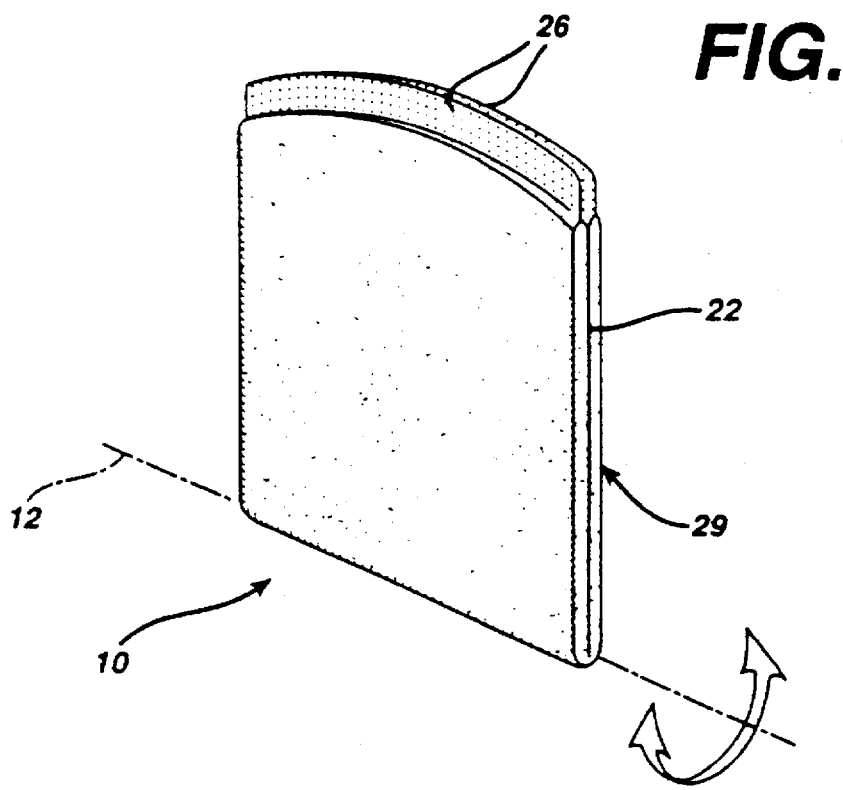
FIG. 4 is a perspective view of a panty liner made in accordance with the present invention in the folded condition, prior to use.

Before use, a panty liner or other absorbent article may be stored in a folded configuration, as illustrated by FIG. 4. Thus, in a preferred embodiment of the articles of this invention, the garment facing side of a panty liner is folded along a transverse central fold line and is brought together into contact with itself. The attachment means register with, or contact only, the release means when the panty liner is folded. No area of the attachment means applied to or located within the attachment zones may contact other attachment means on the garment facing side of the article. If the attachment means contacted one another, the user would be unable to unfold the article without difficulty. When the article is unfolded just prior to its application to the undergarment, the attachment means are exposed to the undergarment surface to which they will be affixed.

In this embodiment, when the panty liner is folded about central fold-line 12 the two transverse ends 26 are parallel and co-extensive. During its preparation for use, panty liner 10 is unfolded by grasping both transverse ends 26 of the liner 10 and pulling the folded liner 10 apart. In order to do this, the user may interpose her fingers between the two transverse ends 26.

Figure 5:
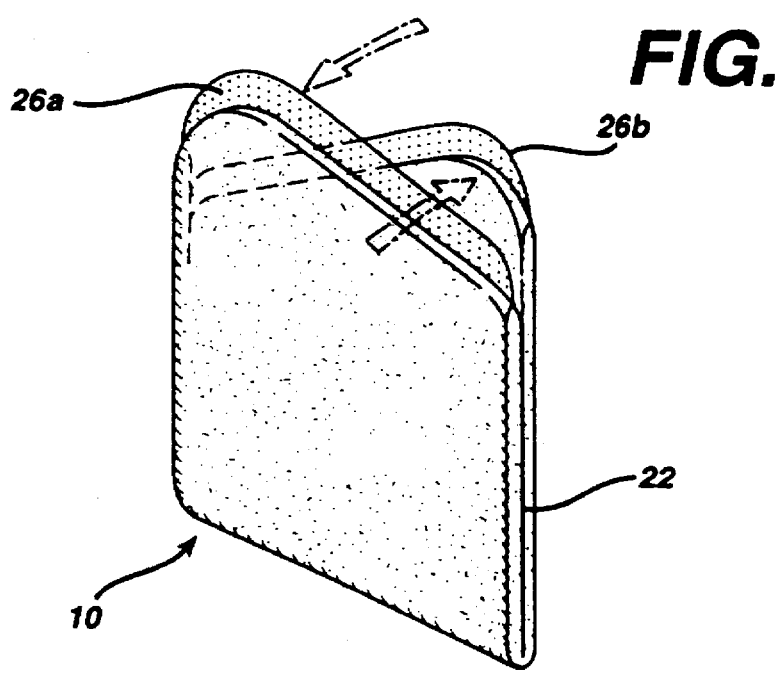
FIG. 5 is a perspective view of an alternate embodiment of the panty liner depicted in FIG. 4.

FIG. 5 illustrates an alternate preferred embodiment of the present invention in a folded configuration. The shape of the panty liner 10 is a parallelogram with oblique angles. When folded, transverse end 26a exposes tab 28a which is the corner formed by the junction of longitudinal edge 27 and transverse end 26a at its highest point measured from the transverse central fold-line 12. The same relationship exists between transverse end 26b and tab 28b. Panty liner 10 may be unfolded by grasping tabs 28a and 28b. The panty liner may be fashioned in the shape of an oblique parallelogram, thus forming the tabs illustrated in FIG. 5. Alternatively, the transverse ends of the liner may be configured in a sine-wave design such that they form rounded tab ends when the liner is folded. Of course, tabs may be created in other forms, so long as they can be individually grasped by the user.

Although three embodiments of the present invention have been illustrated and described in detail, the present invention is in no way so limited. One of ordinary skill will immediately appreciate that the present invention has application to numerous other absorbent articles in addition to the panty liner illustrated. Moreover, the present invention may also be used to eliminate release paper from absorbent articles which are folded along one or more fold lines including those other than the transverse central fold-line.

There are a variety of methods by which the absorbent products of this invention may be made. Preferably, an appropriate barrier film is first printed with a silicone release coating in the release zone. The release coating is cured and adhesive is applied to the attachment zones disposed on the same side as the silicone. Adhesive is also coated on the absorbent facing side of the barrier film to help laminate the film to the absorbent. The adhesive in the attachment zones is preferably applied so as not to occupy the entire surface area of the attachment zones. This provides a tolerance for slight errors in placement of the attachment means in the attachment zone while still substantially guaranteeing the attachment means will lie entirely within the attachment zone. The attachment means is preferably smaller in area than the release means. This allows a tolerance for slight errors in folding the product while substantially guaranteeing the attachment means will be covered by the release means.

The latter side is then affixed to an absorbent substrate, leaving the release coating and adhesive exposed to form the garment facing side of the absorbent article. The finished article is then folded along at least one fold line. The release means and adhesive means contact each other so that the article may be unfolded prior to use without the adhesive means bonding to itself or to the barrier film. The release means may overlap, but the adhesive means must substantially contact only the release means.

For many barriers, treatment is preferred in most cases to impart a low-peel strength surface in the release zones. Silicone-based release agents are excellent for this purpose; these compounds can be applied using many processes other than the screen print/ultraviolet cure set forth below in the Example. In addition to silicon-based release agents, other types of release coats may be used including paraffin waxes, non-stick coatings, varnishes and others known to those of skill in the art. Some types of adhesives become non-tacky when dried or cooled (such as non-pressure sensitive hot melt adhesives or cold glues) and may make suitable release means if used as a coating in the release zone.

Various silicone curing methods may be used, including in addition to ultraviolet curing, heat curing or electron beam curing. The release coating may be applied using a wide variety of coating equipment. Direct and reverse gravure coaters, three-roll offset coaters, smooth five-roll coaters, or ink jet printing are just a few of the possible equipment types contemplated for use in the present invention.

The following Example further illustrates the preferred embodiments of the present invention:

EXAMPLE

A panty liner according to this invention was made as follows. A roll of barrier film of 1.5 mil white microembossed polyethylene film Type #EMB533 available from Exxon Corporation, is first slit to about a 6.125" width. The film was corona treated by the manufacturer prior to slitting to have a surface energy of about 38 dynes/cm on the side which was to be coated. Silicone was then printed in the three strip configuration shown in FIG. 1 on the corona-treated side. The silicone was printed using a screen printer manufactured by Kraemer Koating, Inc. (Serial No. 1036, Toms River, N.J.). The printed strips of silicone were continuous along the length of the roll and about 0.7" wide, separated from one another by a space of about 0.7". The pattern was positioned so that one edge of the middle silicone strip was coextensive with the longitudinal centerline of the film. The longitudinal centerline of the film in its rolled-good state eventually became the transverse centerline of the absorbent product. This is because the product in this example was fabricated so that the length of the product ran transversely across the width of the film.

An ultraviolet (UV) curable type silicone release agent was used, which is made by the General Electric Corporation. The formula is as follows:

| Percent | Product # | Description |
| --- | --- | --- |
| 98% | UV9300* | UV-curable silicone |
| 2% | UV9310C* | UV-activated catalyst |

*General Electric Product Designations

The silicone release agent was added behind a doctor blade inside the printing screen using a low volume metering pump, such as the variable speed pump manufactured by Ismatec. (Model No. 7617-60, made in Switzerland by ISMATEC SA, Zurich, Switzerland). The printing screen used in this example was made by New England Rotary Screen, Inc. (Fall River, Mass.). A 125 mesh Pantene screen has been found to perform best, producing an even coating. The coat weight of the silicone was about 3.4 grams/meter$^2$ (g/m$^2$). It should be noted, however, that the added coating weight can be reduced greatly with more carefully designed equipment. Ideally, only enough silicone should be applied to impart consistent release characteristics to the coated area.

The silicone release material was then cured using the Mini-Conveyorized UV Curing System from American Ultraviolet Company (Murray Hill, N.J.). A lamp setting of 300 watts/inch provided adequate curing over a wide range of speeds, up to almost 400 feet/minute. The optimum machine speed using the materials and equipment of this Example is about 200 feet/min. The curing step fixes the silicone in the release zone thereby preventing transfer of silicone to the adhesive means.

After the silicone was printed and cured onto the barrier film, adhesive was applied. The adhesive was applied within the attachment zones. Preferably the adhesive is not applied to the entire area of the attachment zones. Applying adhesive means onto a smaller area than the whole of the attachment zone, makes registration of the adhesive means easier within the attachment zone. Generally, creating release means which is larger than the adhesive means area is preferred, because this allows for folding error tolerance.

In this Example, the adhesive was applied after the silicone coating, on a separate adhesive coating apparatus. Yet, both the silicone release coating and adhesive could be applied in sequence on the same machine. The adhesive used in this example was HM-1972 hot melt adhesive from H. B. Fuller Company (St. Paul, Minn.). The adhesive was applied at coating weight of about 71 mg/inch$^2$ in three zones. Lower coating weights may also be used as long as there is an amount of adhesive sufficient to hold the product in place during use. For the application of this Example, these strips were about one-half inch wide, about 1.6 inches long and separated by about 0.9 inch spaces between them. The adhesive was applied to release paper and transferred to the film, the release paper being left in place to aid in rewinding the coated film. The head of the adhesive nozzle was fashioned to produce all three adhesive areas at once. The head was alternately turned on and off to provide enough space between the sets of adhesive areas to fashion individual products.

In order to affix the barrier film to an absorbent core or substrate, the same adhesive was be sprayed onto the absorbent-facing side of the barrier film to be used as a laminating adhesive. The adhesive may also be extruded onto the absorbent-facing side of the barrier film. Release papers were used to cover the laminating adhesive as well to aid winding the barrier film into rolls. The release papers were discarded when the product was assembled. Release papers are needed here only by virtue of the manual process herein described. No processing release paper would be required if all the steps of the process are performed on the same machine.

A section of approximately 1.8" was cut transversely across the width of the film. The section was chosen so the adhesive was centered with respect to the width of the 1.8" by 6.125" barrier film section. One edge of the center release strip was still centered with respect to the length of the 6.125" section (formerly the longitudinal centerline of the film in its rolled-good state). The former longitudinal centerline of the rolled-good film now becomes the transverse centerline of the absorbent product.

The laminating adhesive was then exposed by removing the release paper and an absorbent batt was placed against the laminating adhesive. For this Example, the absorbent core or substrate was a co-form of pulp and thermoplastic fiber substantially similar to that used in the CAREFREE PANTY SHIELDS® brand of panty liners manufactured by Personal Products Company of Milltown, N.J. The absorbent was fashioned as a 4.25" width material C-folded around a 1.8 inch insert of the same material. The final width dimension of the absorbent was approximately 2.0". The composite of barrier and absorbent was then crimped on the ends using a knurled block which is hot pressed into the product ends. The product ends were then cut to provide a rounded tab end.

The remaining release paper which covered the adhesive applied to the garment facing side was then removed and the article folded in half along the central fold-line aligned transversely across the napkin, as shown in FIG. 4. The adhesive means contacted the strips of release coating, allowing the product to be easily unfolded without damage or the need to discard a release paper.

The present invention is not limited to the Example and embodiments set forth above. As will be understood by those of ordinary skill in the art, alternate embodiments, variations and modifications of the present invention are possible.

Accordingly, reference should be made to the appended claims to ascertain the full scope of the present invention.

What is claimed is:

1. A method of packaging an absorbent article capable of being affixed to a user's undergarment comprising the steps of:

(a) providing an absorbent substrate having an absorbent side and a barrier side, opposite said absorbent side;

(b) creating attachment means in attachment zones on the barrier side;

(c) creating release means in release zones on the barrier side;

(d) folding the article wherein the attachment means releasably bonds with at least a portion of the release means;

such that said release means protects the attachment means prior to use, and said article may be unfolded without damaging said article, said release means or said attachment means; thereby allowing the attachment means to secure the absorbent article to the user's undergarment.

2. The method of claim 1, further comprising the step of applying a release means comprising a release agent to the barrier side of the absorbent article, such that the attachment means releasably bonds with at least a portion of the release agent when the article is folded prior to use.

3. The method of claim 1 wherein the step of creating attachment means comprises applying a pressure sensitive adhesive on the barrier side.

* * * * *